US00PP27306P3

(12) United States Plant Patent
Suphachadiwong

(10) Patent No.: US PP27,306 P3
(45) Date of Patent: Oct. 25, 2016

(54) ***VANDA* PLANT NAMED 'SPCDW1319'**

(50) Latin Name: ***Vanda* hybrid**
Varietal Denomination: SPCDW1319

(71) Applicant: Thumrong Suphachadiwong, Chonburi (TH)

(72) Inventor: Thumrong Suphachadiwong, Chonburi (TH)

( * ) Notice: Subject to any disclaimer, the term of this patent is extended or adjusted under 35 U.S.C. 154(b) by 88 days.

(21) Appl. No.: 14/544,029

(22) Filed: Nov. 17, 2014

(65) Prior Publication Data

US 2015/0143595 P1 May 21, 2015

(30) Foreign Application Priority Data

Nov. 19, 2013 (QZ) ..... PBR 2013/2928

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Samuel R. McCoy, Jr.

(57) ABSTRACT

'SPCDW1319' is a distinctive variety of *Vanda* which is characterized by white sepal and petal coloration with pink dots and blurs, as well as the stability and uniformity of traits through successive cycles of asexual propagation.

3 Drawing Sheets

Latin name of the genus and species: The Latin name of the genus and species of the novel variety disclosed herein is *Vanda* hybrid.

Variety denomination: The inventive variety of *Vanda* disclosed herein has been given the variety denomination 'SPCDW1319'.

BACKGROUND OF THE INVENTION

This application relates to a new cultivar of *Vanda*, as described in EU application number 2013/2928, filed Nov. 19, 2013, grant pending, to which applicant claims priority.

Parentage: The *Vanda* variety 'SPCDW1319' is the result of a planned breeding program. The new variety originated as a seedling from the crossing of the unpatented, proprietary seed parent *Vanda* 'K74' with the unpatented, proprietary pollen parent referred to as *Vanda* 'M166'. The crossing was made by the inventor in his research greenhouse in Chonburi, Thailand in September of 2002.

The new variety was first selected by the inventor, Thumrong Suphachadiwong, a citizen of Thailand, in October 2007, in a research greenhouse belonging to the inventor in Chonburi, Thailand. After identifying the new variety as a potentially interesting selection, the inventor continued confidential testing and propagation of 'SPCDW1319', assessing stability of the unique characteristics of this variety.

Asexual Reproduction: Asexual reproduction of the new cultivar 'SPCDW1319' was first performed at a commercial laboratory belonging to the inventor in Chonburi, Thailand by tissue culture in November of 2007. Access to all plants was restricted, as plants were kept in a greenhouse not open to the public, and tissue culture plantlets were in a laboratory belonging to the inventor, and not accessible to the public. Through subsequent propagation by vegetative cuttings, multiple generations have been reproduced, which have shown that the unique features of this cultivar are stable and reproduced true to type.

SUMMARY OF THE INVENTION

The cultivar 'SPCDW1319' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1319'. These characteristics in combination distinguish 'SPCDW1319' as a new and distinct *Vanda* cultivar:

1. Unique sepal and petal coloration of pink dots and blurs with white; and,
2. Unique pink color pattern of sepals and petals; and,
3. Improved plant compatibility for commercial growing methods; and,
4. Pink floral lip.

BOTANICAL DESCRIPTION OF THE PLANT

Figure 1:
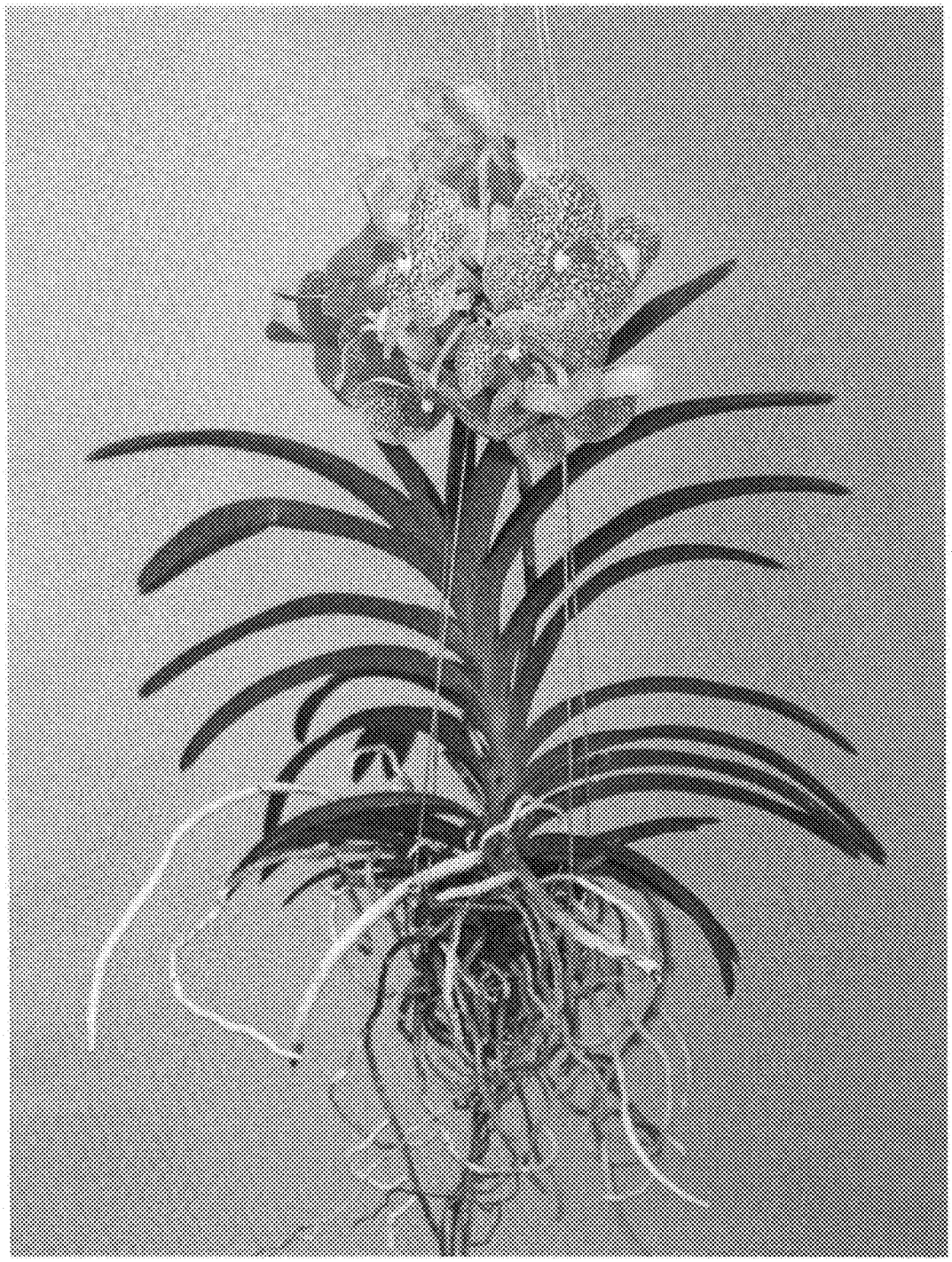
FIG. 1 illustrates, as nearly true as it is reasonably possible to make the same in color photographs of this type, an exemplary plant of 'SPCDW1319' grown in a commercial greenhouse in Honselersdijk, the Netherlands. This plant is approximately 5.5 years old, shown planted in an 8 by 8 cm container.
Figure 2:
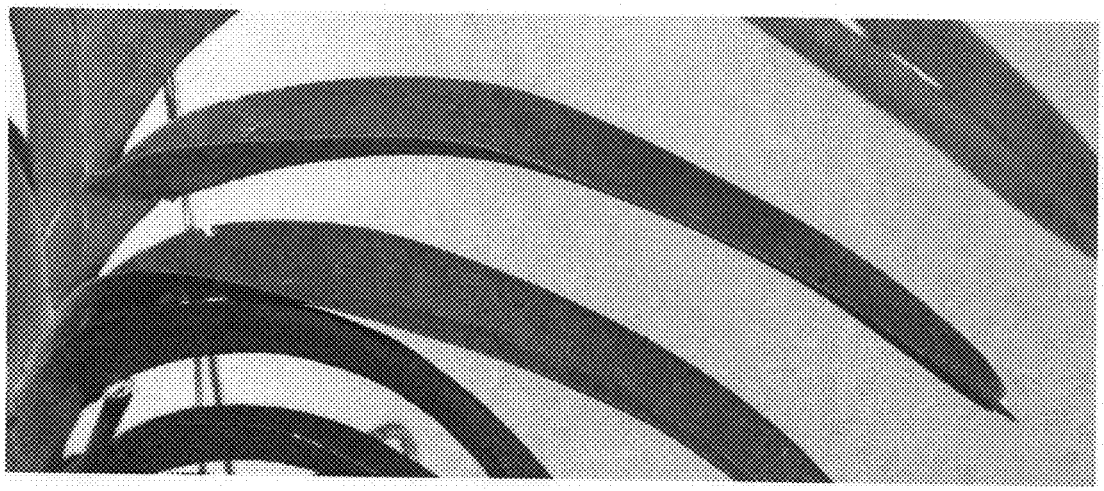
FIG. 2 illustrates, in full color, the typical foliage of 'SPCDW1319'.
Figure 3:
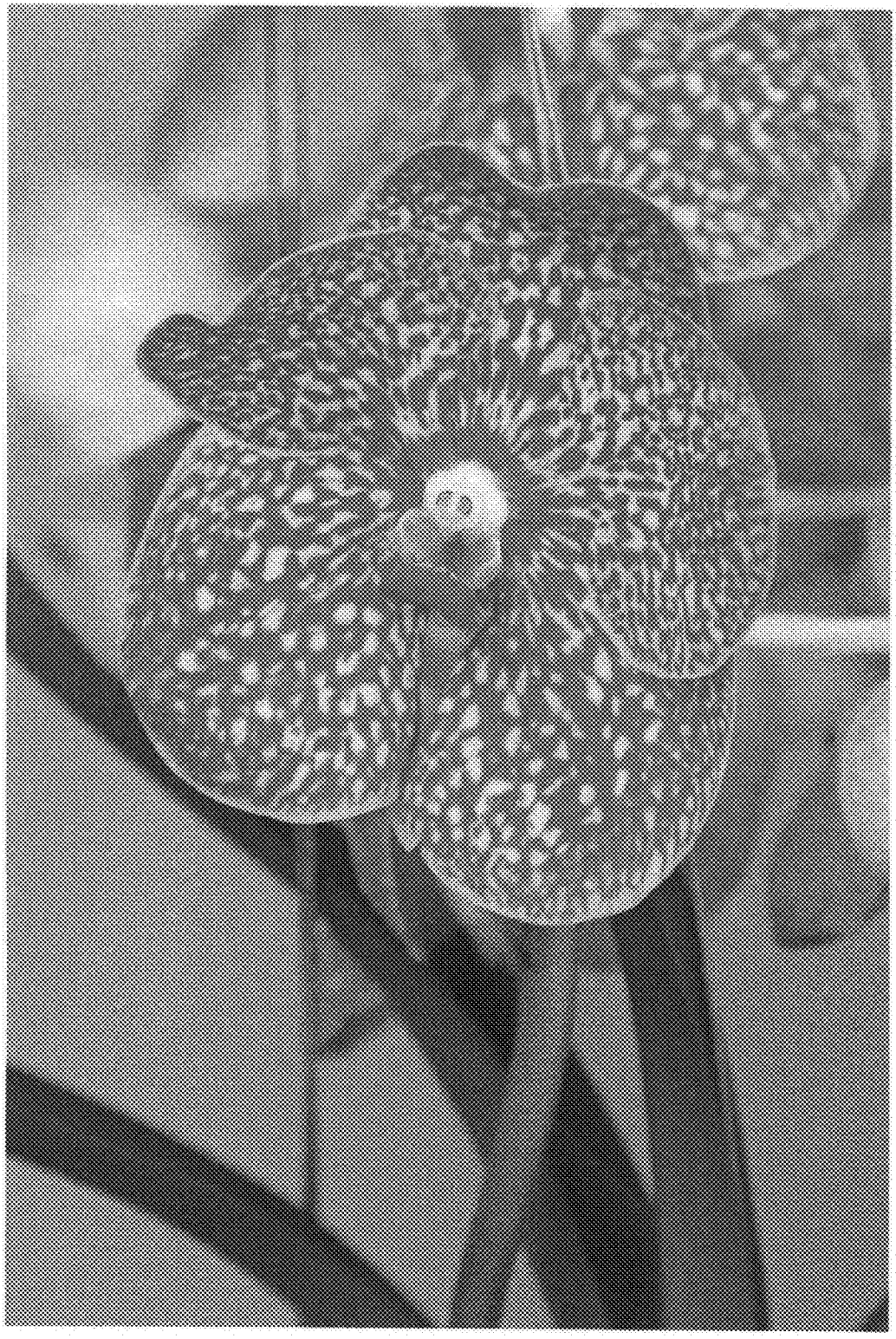
FIG. 3 illustrates, in full color, the typical flowers of 'SPCDW1319'.

The following observations and measurements describe 'SPCDW1319' plants grown in a greenhouse in Honselersdijk, the Netherlands. Temperatures ranged were approximately 23 degrees Celsius during the day and 19 degrees Celsius at night. No photoperiodic or chemical treatments were given to the plants. When natural lighting fell below 150 Watt, artificial lighting is given at 10,000 lux for 16 hours a day. Measurements and numerical values represent averages of typical plant types.

Those skilled in the art will appreciate that certain characteristics will vary with older or, conversely, with younger plants. 'SPCDW1319' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2007 edition.

A botanical description of 'SPCDW1319' and comparisons with other varieties of *Vanda* are provided below.

TECHNICAL DESCRIPTION OF THE VARIETY

Plant description:

*Growth habit*.—Monopodial, upright.

*Average height from base (plant grown in hanging basket, so no soil line present) to top of foliage*.—32.2 cm.

*Average height from base (plant grown in hanging basket, so no soil line present) to top of flowers*.—40.5 cm.

*Plant spread*.—Average of 40.5 cm.

*Normal pot size*.—Hanging basket (8 by 8 cm square).

*Growth rate*.—Moderate.

*Number of leaves per plant*.—Average of 26.

*Propagation type*.—Tissue Culture.

*Propagation details*.—The time needed from for the start of a mericlone to get the small plants ready for deflasking is approximately 24 months under a controlled temperature of about 26 degrees Celsius. After that period plants have matured roots. Plants start to make roots in the last 6 months in flasks. After deflasking they remain in a shaded and controlled environment.

*Disease resistance*.—Good resistance to the normal diseases found in *Vanda*.

*Drought tolerance and cold tolerance*.—Drought tolerance is typical for species. Superior cold tolerance, to approximately 6 degrees Celsius.

Root system: Moderately to heavy rooting with aerial roots only. Roots very fleshy, non-fibrous. Average length of old roots is 31.2 cm, average diameter of old roots is 0.3 cm, average diameter of young roots is 0.8 cm. Old roots colored yellow-green; near RHS 146D. Young roots colored greyed-green; near RHS 192B to 192C, growing tips of roots yellow-green; 144A.

Foliage:

*Arrangement*.—Distichous.

*Average length*.—Approximately 20.7 cm.

*Average width*.—Approximately 2.6 cm.

*Shape of blade*.—Ligulate, strongly carinate.

*Aspect*.—Moderately curved.

*Apex*.—Unequal to unequal emarginated and unequal praemorse.

*Base*.—Sheathing.

*Sheath length*.—Average 1.9 cm.

*Sheath width*.—Average 1.5 cm.

*Sheath color*.—Yellow-green; near RHS 144B.

*Margin*.—Entire.

*Texture of top surface*.—Glabrous, very slightly glossy.

*Texture of bottom surface*.—Glabrous, matte.

*Color of young foliage, upper side*.—Green; near RHS 143A.

*Color of young foliage, under side*.—Yellow-green; near RHS 144A.

*Color of mature foliage, upper side*.—Green to yellow-green; in between near RHS N137D and 147A.

*Color of mature foliage, under side*.—Yellow-green; near RHS 146A.

*Venation*.—Parallel.

*Venation coloration*.—As leaf surface; upper side green to yellow-green; in between near RHS N137D and 147A, lower side yellow-green; near RHS 146A.

*Petiole*.—No petioles present, leaves sessile.

Inflorescence:

*Flowers per stem*.—Average of 15.

*Inflorescence arrangement*.—Axially placed raceme.

*Inflorescence height*.—Approximately 28.3 cm (measured from base of lowest flower to top of upper flower).

*Inflorescence width*.—Approximately 15.9 cm.

*Peduncle*.—Length — Approximately 40.0 cm. Width — Approximately 0.7 cm. Aspect — Approximately 25° angle to rosette. Strength — Strong. Texture — Smooth, moderately glossy. Color — Yellow-green; near RHS 144A.

Bud:

*Rate of opening*.—Buds open approximately three weeks from first sight.

*Length*.—Average of 1.7 cm.

*Diameter*.—Average of 1.6 cm.

*Shape*.—Broad obovate.

*Color*.—Purple; near RHS 76C, base violet; near RHS 84D.

Flower:

*Flower type*.—Zygomorphic (orchidaceous), typical shape for the genus *Vanda*.

*Shape*.—Zygomorphic, consisting of three sepals and three petals, one of which is transformed into a labellum (lip).

*Length (height)*.—Approximately 10.1 cm.

*Width*.—Approximately 9.8 cm.

*Depth*.—Approximately 3.6 cm.

*Fragrance*.—No fragrance.

*Lastingness*.—6 to 8 weeks, depending on growing conditions.

*Persistent*.—No.

*Quantity of petals*.—3 (2 "traditional" petals and a labellum (lip), described separately).

*Petals*.—Arrangement — one lateral petal on each side. Length — Approximately 4.8 cm. Width — Approximately 4.5 cm. Shape — Near orbicular to broad ovate. Apex — Obtuse. Base — Cuneate. Margin — Entire. Texture of Upper forward surface — Glabrous, matte, velvety. Texture of Lower back surface — Glabrous, matte, velvety. Color When opening, forward surface — Purple to white; in between near RHS 76D and NN155D, dotted Red-purple; near RHS 72B. Color When opening, back surface — Purple to white; in between near RHS 76D and N155A, dotted Red-purple; near RHS 77D. Color When Fully Opened, forward surface — White; near RHS NN155D, heavily dotted red-purple to purple; in between near RHS N74A and N78A. Color When Fully Opened, back surface — Purple to white; in between near RHS 76D and N155A, heavily tinged purple; N78D, especially towards the margins and top. Fading, forward surface — Not fading. Fading, back surface — Not fading. Color Venation Fully Opened, forward surface — Veins not visible, colored as petal surface. Color Venation Fully Opened, back surface — Main vein purple; N78D, other veins as petal surface.

*Labellum/lip*.—Shape — Three-lobed, lateral lobes involute, central lobe slightly revolute. Length — Approximately 2.0 cm (excl. spur). Width — Approximately 1.4 cm. Texture — Glabrous, slightly glossy, with 3 callosities. Apex — Emarginate. Base — Cuneate. Color When Opening, forward surface — Lateral lobes violet; near RHS 84C, striped and blotched purple; near RHS N78A to N78B. Central lobe purple; near RHS N78A with a lighter base; near RHS N78B to N78C, callosities white; near RHS N155A. Color When opening, back surface — Lateral lobes purple; near RHS 75D. Central lobe purple; near RHS N78A, base lighter; near RHS 75C and 75D. Color When Fully Opened, forward surface — Lateral lobes violet; near RHS 84B to 84C, striped and blotched purple; near RHS N78A to N78B. Central lobe purple; near RHS N78A with a lighter base; near RHS N78B to N78C, callosities white; near RHS N155A. Color When Fully Opened, back surface — Lateral lobes purple; near RHS 75D. Central lobe purple; near RHS N78A, base lighter; near RHS 75C and 75D. Fading, forward surface — Not fading. Fading, back surface — Not fading. Color Venation Fully Opened, forward surface — No venation visible on labellum. Color Venation Fully Opened, back surface — No venation visible on labellum. Margin — Entire.

*Spurs*.—Quantity — Average of 1. Appearance — Short triangular, in line with central lobe of labellum. Length — Approximately 0.9 cm. Width — Approximately 0.35 cm. Height — Approximately 0.6 cm (at the base). Shape — Short triangular. Apex — Obtuse. Base — Broad cuneate. Margin — Entire. Texture — Glabrous, very slightly glossy. Color — Purple; near RHS 76D, tip darker; near RHS 76B to 76C.

*Sepals*.—Quantity — Average of 3. Appearance — One dorsal sepal (pointing upright) and two lateral sepals. Length — Dorsal sepal approximately 5.1 cm and lateral sepals approximately 5.3 cm. Width — Dorsal sepal approximately 5.0 cm and lateral sepals approximately 5.2 cm. Shape — Dorsal sepal broad ovate. Lateral sepals near orbicular to reniform. Apex — Obtuse. Base — Cuneate. Margin — Entire. Texture — Glabrous, matte, velvety. Color — Dorsal sepal and lateral sepals white; near RHS NN155D, heavily dotted red-purple to purple; in between near RHS N74A and N78A.

*Pedicels*.—Length — Approximately 5.8 cm. Diameter — Approximately 0.4 cm. Angle — Approximately 70° angle to peduncle. Strength — Very strong. Texture — Glabrous, axially angled with 5 "ribs", axially twisted (due to resupination), glossy. Color — Purple; near RHS 76C, tinged white; near RHS 155C towards distal end, tinged white; near RHS NN155A towards proximal end.

Reproductive organs: Stamens, style and stigma fused into column? Yes.

*Column length*.—Approximately 0.6 cm.

*Column diameter*.—Approximately 0.7 cm.

*Column color*.—White; near RHS NN155D.

*Ovary position*.—Inferior.

*Ovary diameter*.—Approximately 0.5 cm.

*Ovary color*.—White; near RHS NN155C.

*Pollen color*.—Yellow-orange; near RHS 15A.

Seed and fruit: Seed production has not been observed.

COMPARISONS WITH PARENT PLANTS

Plants of the new cultivar 'SPCDW1319' are similar to the seed parent, *Vanda* 'K74' in most horticultural characteristics. However, the new variety exhibits white flowers that are heavily dotted pink, whereas the seed parent exhibits cream to yellow flowers with red spots.

Plants of the new cultivar 'SPCDW1319' are similar to the pollen parent, *Vanda* 'M166' in most horticultural characteristics. Plants of the new variety, however, are larger, with a longer leaf span than the pollen parent.

COMPARISONS WITH OTHER COMMERCIAL *VANDA*

'SPCDW1319' is similar in most horticultural characteristics to the commercial variety *Vanda* 'Blue Magic' (not patented). The new variety, however, produces sepals and petals colored white with pink dots and blurs whereas 'Blue Magic' produces petals and sepals that are white with thick, dark purple netting. The new variety has flowers which are similar in size as 'Blue Magic'.

That which is claimed is:

1. A new and distinct variety of *Vanda* plant named 'SPCDW1319', substantially as described and illustrated herein.

* * * * *